(12) United States Patent
Wiederin et al.

(10) Patent No.: US 10,399,099 B1
(45) Date of Patent: Sep. 3, 2019

(54) SYSTEMS AND METHODS FOR AUTOMATIC ADJUSTMENT OF MIXED GAS FLOW FOR AN INJECTOR COORDINATED WITH THE ACQUISITION OF PARTICULAR GROUPS OF CHEMICAL ELEMENTS FOR ANALYSIS

(71) Applicant: Elemental Scientific, Inc., Omaha, NE (US)

(72) Inventors: Daniel R. Wiederin, Omaha, NE (US); Kevin Wiederin, Omaha, NE (US)

(73) Assignee: ELEMENTAL SCIENTIFIC, INC., Omaha, NE (US)

(*) Notice: Subject to any disclaimer, the term of this patent is extended or adjusted under 35 U.S.C. 154(b) by 179 days.

(21) Appl. No.: 15/590,700

(22) Filed: May 9, 2017

Related U.S. Application Data

(60) Provisional application No. 62/333,375, filed on May 9, 2016.

(51) Int. Cl.
  *B05B 7/00* (2006.01)
  *G01N 30/04* (2006.01)
  *H01J 49/00* (2006.01)
  *H01J 49/04* (2006.01)

(52) U.S. Cl.
  CPC .......... *B05B 7/0012* (2013.01); *G01N 30/04* (2013.01); *H01J 49/0045* (2013.01); *H01J 49/045* (2013.01)

(58) Field of Classification Search
  None
  See application file for complete search history.

(56) References Cited

U.S. PATENT DOCUMENTS

2008/0035844 A1* 2/2008 Sakata ................. H01J 49/105
                                                              250/288

* cited by examiner

*Primary Examiner* — Kathryn Wright
(74) *Attorney, Agent, or Firm* — Kevin E. West; Advent, LLP

(57) ABSTRACT

Systems and methods are described for automatically adjusting the composition of a spray chamber matrix gas flow coordinated with an analysis of a particular chemical element or groups of elements. A system can include a spray chamber configured to be coupled to an analytical system, the spray chamber having a nebulizer gas port configured to receive a nebulizer gas; and an inlet for receiving a gas from at least one gas source. The system also includes a controller operably coupled to the spray chamber, the controller configured to adjust a gas flow rate of the gas from the at least one gas source in coordination with analysis of a particular chemical element by the analytical system.

19 Claims, 2 Drawing Sheets

| Chemical Element | Plasma Conditions | Spray Chamber Matrix Gas | Reaction Cell Gas |
|---|---|---|---|
| Arsenic (As) | Hot | Nitrogen (N$_2$) | Ammonia (NH$_3$) |
| Iron (Fe) | Cold | None | Ammonia (NH$_3$) |
| Sodium (Na) | Cold | None | None |
| Potassium (K) | Cold | None | Ammonia (NH$_3$) |
| Tungsten (W) | Hot | Nitrogen (N$_2$) | None |

SYSTEMS AND METHODS FOR AUTOMATIC ADJUSTMENT OF MIXED GAS FLOW FOR AN INJECTOR COORDINATED WITH THE ACQUISITION OF PARTICULAR GROUPS OF CHEMICAL ELEMENTS FOR ANALYSIS

CROSS-REFERENCE TO RELATED APPLICATIONS

The present application claims the benefit under 35 U.S.C. § 119(e) of U.S. Provisional Application Ser. No. 62/333,375, filed May 9, 2016, and titled "SYSTEMS AND METHODS FOR AUTOMATIC ADJUSTMENT OF MIXED GAS FLOW FOR AN INJECTOR COORDINATED WITH the ACQUISTION OF PARTICULAR GROUPS OF CHEMICAL ELEMENTS FOR ANALYSIS." U.S. Provisional Application Ser. No. 62/333,375 is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods are described for automatically adjusting the composition of a mixed gas flow of an injector, where the composition is coordinated with the acquisition of particular groups of chemical elements during analysis, such as a sample analysis via ICP-MS. A system can include a spray chamber configured to be coupled to an analytical system, the spray chamber having a nebulizer gas port configured to receive a nebulizer gas; and an inlet for receiving a gas from at least one gas source. The system also includes a controller operably coupled to the spray chamber, the controller configured to adjust a gas flow rate of the gas from the at least one gas source in coordination with analysis of a particular chemical element by the analytical system.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

DETAILED DESCRIPTION

Overview

Sample processing conditions can affect the sensitivity of measurements of differing chemical elements. Particular processing conditions can benefit the sensitivity of measurement of a chemical element or groups of elements while not benefitting or even worsening the sensitivity of measurement of other elements or groups of elements. For example, differing spray chamber matrix gases or compositions, differing plasma condition types (e.g., cool plasma, hot plasma, etc.), differing cell gas compositions, or the like can affect the sensitivity of differing chemical elements in different manners. Thus, for a single sample, a variety of processing conditions can benefit analysis of each chemical element of a plurality of chemical elements that may be present in that sample.

In one aspect, the present disclosure is directed to a sample preparation system that automatically adjusts the composition of a gas flow, such as one introduced to a spray chamber or an injector, to be coordinated with an analysis of a particular chemical element or groups of elements. For example, a spray chamber matrix gas flow (e.g., nitrogen ($N_2$), hydrogen ($H_2$), organic gas, or other gas component) can be adjusted in combination with a nebulizer gas flow (e.g., Argon (Ar)), such that the spray chamber matrix gas flow is mixed with the nebulizer gas flow during periods of time when an element or group of elements is measured where such measurement benefits from the presence of the spray chamber matrix gas, and the spray chamber matrix gas flow is not present or is present at a reduced flow rate when an element or group of elements is measured where such measurement does not benefit from the presence of the spray chamber matrix gas. In implementations, the sample preparation system can control gas flows from multiple gas sources to manage the flow and composition of the spray chamber matrix gas in coordination with multiple types of analyses to measure a plurality of chemical species.

Example Implementations

Figure 1:
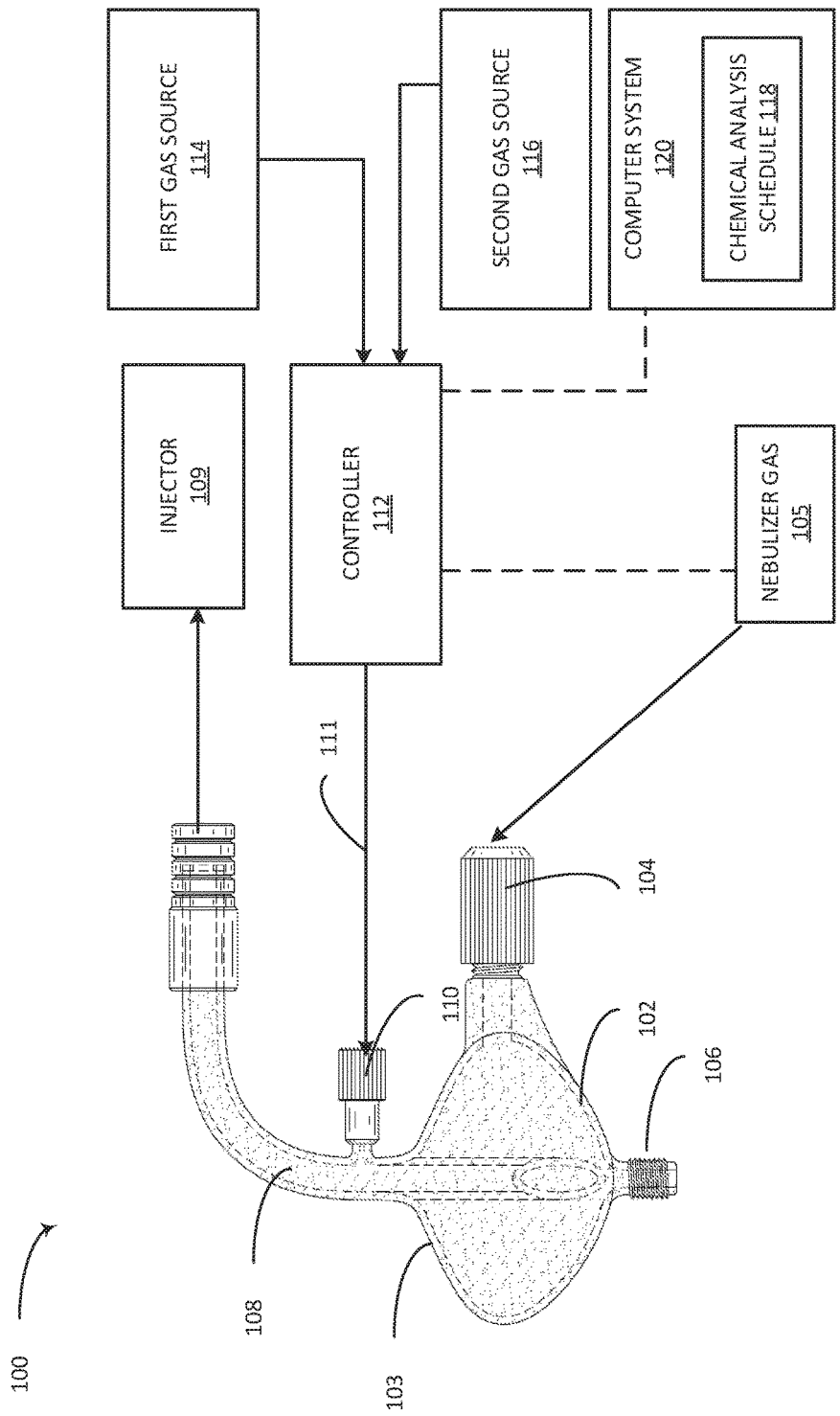
FIG. 1 is a diagrammatic illustration of a system for automatically adjusting the composition of a spray chamber matrix gas flow coordinated with an analysis of a particular chemical element or groups of elements, in accordance with example implementations of the present disclosure.

Referring generally to FIG. 1, a system 100 is shown that automatically changes or adjusts the composition a gas flow, coordinated with an analysis of a particular chemical element or groups of elements. The system 100 includes a spray chamber 102 having a nebulizer gas port 104 configured to receive a nebulizer gas flow 105, a drain port 106 (e.g., to drain waste droplets from the spray chamber 102), and an exit port 108 configured to connect to an injector 109, such as an ICPMS injector configured to couple with an ICPMS torch. For example, the exit port 108 can be a fluid line coupled between a body portion 103 of the spray chamber 102 (e.g., into which the nebulizer gas flow 105 is introduced via the nebulizer gas port 104) and the injector 109. The exit port 108 is in fluid communication with an inlet 110 coupled to a gas addition line 111 to introduce one or more gases to a fluid stream exiting the body portion 103 of the spray chamber 102 via the exit port 108 which can provide a mixed gas stream to the injector 109. For example, the fluid stream exiting the body portion 103 of the spray chamber 102 can include the nebulizer gas 105, an aerosolized sample, a combination of the nebulizer gas 105 and aerosolized sample, etc. The one or more gases supplied to the inlet 110 can include gases to influence the sensitivity of measurements of particular chemical elements or groups of elements during analysis the mixed gas stream. In implementations, the gas supplied to the inlet 110 includes a spray chamber matrix gas, including but not limited to, one or more of nitrogen ($N_2$), hydrogen ($H_2$), organic gas (e.g., volatile organic compound (VOC)), or other gas introduced to influence the sensitivity of measurements of chemical elements during quantitative analysis.

The inlet 110 is coupled with a controller 112 (e.g., via the gas addition line 111) to regulate the flow of one or more gas flows to the inlet 110. FIG. 1 shows the controller 112 coupled with a first gas source 114 and a second gas source 116, however more (e.g., three, four, or more) or fewer gas sources can be employed. The controller 112 can include but is not limited to, one or more of a multi-port valve switchable between at least two operating positions, a flow controller (e.g., one or more mass flow controllers), or other flow control device to regulate the flow of gas from the coupled gas sources (e.g., the first gas source 114 and the second gas source 116). For example, the controller 112 can vary the flow rate of a particular gas introduced to the inlet 110, such as by increasing or decreasing the flow rate of the particular gas. In implementations, the controller 112 can toggle which gas of a plurality of gases is introduced to the inlet 110. For example, in the controller 112 can include a first configuration to permit the flow of the first gas from the first gas source 114 to the inlet 110 while preventing the flow of the second gas from the second gas source 116 from flowing to the inlet 110. The controller 112 can include a second configuration to permit the flow of the second gas from the second gas source 116 to the inlet 110 while preventing the flow of the first gas from the first gas source 114 from flowing to the inlet 110. The controller 112 can include a third configuration to prevent the flow of the first gas from the first gas source 114 from flowing to the inlet 110 and to prevent the flow of the second gas from the second gas source 116 from flowing to the inlet 110. The controller 112 can include a fourth configuration to permit the flow of the first gas from the first gas source 114 to the inlet 110 and to permit the flow of the second gas from the second gas source 116 to the inlet 110. In implementations, the controller 112 can independently control the flow rates of a plurality of gases introduced to the inlet 110. For example, the controller 112 can independently maintain, increase, or decrease the flow rate of the first gas from the first gas source 114 while maintaining, increasing, or decreasing the flow rate of the second gas from the second gas source 116.

The controller 112 is configured to operate in coordination with the type of chemical element or group of elements being analyzed for a given sample. For example, the spray chamber 102 can be coupled with an ICP-MS analytical instrument (e.g., via an injector/torch coupled to the exit port 108) to analyze a plurality of chemical elements present in a given sample. The operating conditions to analyze a first element may not be beneficial, or may even be detrimental, to analysis of a second element. For example, introduction of nitrogen ($N_2$) can aid in improving the sensitivity of arsenic (As) measurements under hot plasma conditions, however for the determination of iron (Fe) under cool plasma conditions, introduction of nitrogen ($N_2$) can provide little to no benefit, or can even be detrimental to the sensitivity of the iron measurement. The controller 112 is configured to initiate or increase the flow rate of one or more gases (e.g., the first gas source 114, the second gas source 116, another gas, etc.) to the inlet 110 during a time period when an analysis of a particular chemical is occurring when the presence of the one or more gases provides increased sensitivity (or is not substantially detrimental) during measurement of the particular chemical. The controller 112 is also configured to stop or decrease the flow rate of one or more gases (e.g., the first gas source 114, the second gas source 116, another gas, etc.) to the inlet 110 during a time period when an analysis of a particular chemical is occurring when the presence of the one or more gases provides little to no sensitivity benefits (or is detrimental) during measurement of the particular chemical. In implementations, the controller 112 is operably coupled to chemical analysis schedule 118 accessible via a computer system 120. The chemical analysis schedule 118 can store a list of chemical analyses to be performed at the analysis system (e.g., the ICP-MS analytical instrument). The controller 112 accesses the chemical analysis schedule to initiate the proper gas flow settings to transfer the gas flow to the inlet 110 under the conditions appropriate for the scheduled chemical analysis. The gas flow settings can include, but are not limited to which source or sources of gas to permit flow (e.g., the first gas source 114, the second gas source 116, each of the first gas source 114 and the second gas source 116, neither of the first gas source 114 or the second gas source 116, etc.), the volumetric flow rate for each gas source, the mass flow rate for each gas source, the operation mode of the torch of the analysis system (e.g., cool plasma conditions, hot plasma conditions, etc.), or the like. For example, the controller 112, the computer system 120, or combinations thereof can store a gas flow setting corresponding to each individual type of chemical analysis such that when the controller 112 accesses the chemical analysis schedule, the controller 112 can initiate the appropriate gas flow setting for the next chemical analysis scheduled, such as through structural rearrangement (e.g., in the case of a multi-port valve to provide fluid communication between a particular gas flow source and the inlet 110), throttling of gas flow (e.g., in the case of a mass flow controller), or the like. An example gas flow setting table 200 is shown with reference to FIG. 2, and is described further herein. In implementations, the chemical analysis schedule 118 and the controller 112 are incorporated into the computer system 120, however, in other implementations, the controller 112 and the computer system 120 are physically separate components which communicate through wireless or wired communication protocols. In implementations, the chemical analysis schedule 118 is stored at the controller 112, where the controller 112 includes a local computer memory device to store the chemical analysis schedule 118 for access by the controller 112.

Figure 2:
FIG. 2 is a diagrammatic illustration of controller operation conditions in coordination with the type of chemical element or group of elements being analyzed for a given sample.

An example implementation of the controller 112 operation in coordination with the type of chemical element or group of elements being analyzed for a given sample is provided in FIG. 2. The gas flow setting table 200 indicates that for an analysis of the sample for arsenic content, the controller 112 permits the flow of nitrogen to the inlet 110 for combination with the nebulizer gas 105 and the aerosolized sample prior to injection. Other analysis conditions for the analysis of arsenic content include hot plasma and ammonia reaction cell gas. For example, the controller 112 can adopt a first configuration to permit the flow of gas from the first gas source 114 (e.g., a nitrogen gas flow), while blocking the flow of gas from the second gas source 116, or any other gas source when the chemical analysis schedule 118 accessed by the controller 112 indicates that an arsenic analysis is scheduled. When the sample is analyzed for iron content (e.g., when the chemical analysis schedule 118 indicates that an iron analysis is scheduled), the controller 112 automatically adjusts the spray chamber matrix gas (e.g., the first gas source 114, the second gas source 116, another gas, etc.) to prevent the flow of spray chamber matrix gas to the inlet 110 while under cool plasma conditions with an ammonia reaction cell gas. When the sample is analyzed for sodium content, the controller 112 automatically adjusts (or maintains) the spray chamber matrix gas (e.g., the first gas source 114, the second gas source 116, another gas, etc.) to prevent the flow of spray chamber matrix gas to the inlet 110 while under cool plasma conditions without an ammonia reaction cell gas. When the sample is analyzed for potassium content, the controller 112 automatically adjusts (or maintains) the spray chamber matrix gas (e.g., the first gas source 114, the second gas source 116, another gas, etc.) to prevent the flow of spray chamber matrix gas to the inlet 110 while under cool plasma conditions with an ammonia reaction cell gas. When the sample is analyzed for tungsten content, the controller 112 automatically adjusts the spray chamber matrix gas to permit the flow of nitrogen gas to the inlet 110 while under hot plasma conditions without an ammonia reaction cell gas.

In implementations, the system 100 automatically coordinates the flow of the spray chamber matrix gas (e.g., the first gas source 114, the second gas source 116, another gas, etc.) with the flow of the nebulizer gas 105 provided to the nebulizer gas port 104. For example, the controller 112 (or another flow controller) can adjust the flow of the nebulizer gas 105 provided to the nebulizer gas port 104 in coordination with the amount of flow of gas provided to the inlet 110. In implementations, the total amount of gas provided to the nebulizer gas port 104 and the inlet 110 is maintained at a constant level (e.g., the amount of gas leaving the exit port 108 remains constant on a volumetric basis, mass basis, or the like), such that when the controller 112 restricts the flow of gas to the inlet 110, the amount of gas supplied to the nebulizer gas port 104 is increased relative to when the controller does not restrict the flow of gas to the inlet 110, where the nebulizer gas flow 105 would be decreased. For example, when the controller 112 accesses the chemical analysis schedule 118 and a chemical analysis is scheduled having a corresponding gas flow setting that does not require a spray chamber matrix gas to inlet 110, the system 100 (via the controller 112 or other flow controller) can increase or maintain the flow of nebulizer gas 105 provided to the nebulizer gas port 104 to maintain the constant amount of gas leaving the exit port 108. When the controller 112 accesses the chemical analysis schedule 118 and a chemical analysis is scheduled having a corresponding gas flow setting that does require a spray chamber matrix gas to inlet 110, the system 100 (via the controller 112 or other flow controller) can decrease or maintain the flow of nebulizer gas 105 provided to the nebulizer gas port 104 to maintain the constant amount of gas leaving the exit port 108. In general, the previous chemical analysis gas flow settings will dictate whether gas flow settings should be altered. For instance, if the previous chemical analysis was an iron content analysis and the next scheduled analysis is a sodium content analysis, then the flow of nebulizer gas 105 provided to the nebulizer gas port 104 may not be altered, since the example gas flow setting table 200 provides for no spray chamber matrix gas for either iron or sodium analyses. The flow rate of the spray chamber matrix gas can be less than the flow rate of the nebulizer gas 105. For example, the flow rate of the spray chamber matrix gas can be from about 1 mL/min to about 100 mL/min, whereas the flow rate of the nebulizer gas 105 can be from about 0.3 L/min to about 1.5 L/min.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
  a nebulizer gas source;
  a first gas source;
  a second gas source;
  a spray chamber configured to be coupled to an analytical system, the spray chamber having
    a nebulizer gas port configured to receive a nebulizer gas from the nebulizer gas source; and
    an inlet configured to receive a gas from at least one of the first gas source and the second gas source; and
  a controller operably coupled to the spray chamber to regulate fluid flow between the inlet of the spray chamber and at least the first gas source and the second gas source, the controller configured to access a memory device storing a chemical analysis schedule storing a list of chemical analyses to be performed by the analytical system, the controller also configured to access a memory device storing a gas flow setting corresponding to each chemical analysis of the list of chemical analyses, the controller configured to adjust a gas flow rate of each of the first gas source and the second gas source according to the gas flow setting in coordination with a next scheduled chemical analysis of the list of chemical analyses.

2. The system of claim 1, wherein the controller is configured to permit flow of a first gas from the first gas source and to prevent flow of a second gas from the second gas source.

3. The system of claim 1, wherein the controller is configured to prevent flow of a first gas from the first gas source and to permit flow of a second gas from the second gas source.

4. The system of claim 1, wherein the controller is configured to prevent flow of a first gas from the first gas source and to prevent flow of a second gas from the second gas source.

5. The system of claim 1, wherein the controller is configured to permit flow of a first gas from the first gas source and to permit flow of a second gas from the second gas source.

6. The system of claim 1, wherein the gas flow setting also includes at least one of a plasma condition type or a reaction cell gas type for a reaction cell of the analytical system.

7. The system of claim 1, wherein the controller is configured to adjust a gas flow rate of the nebulizer gas to the nebulizer gas port.

8. The system of claim 1, wherein the controller is configured to adjust a gas flow rate of the nebulizer gas to the nebulizer gas port in coordination with regulation of fluid flow between the inlet of the spray chamber and at least the first gas source and the second gas source to maintain a constant gas flow rate leaving the spray chamber.

9. The system of claim 8, wherein the gas flow rate of the nebulizer gas is higher than a gas flow rate of gas received by the inlet.

10. The system of claim 1, wherein the controller is operably coupled to at least one of a multiport valve or a mass flow controller.

11. A method for controlling a composition of gas introduced to an analytical system, the method comprising:
providing a system, the system including a nebulizer gas source;
a first gas source;
a second gas source;
a spray chamber configured to be coupled to an analytical system, the spray chamber having
a nebulizer gas port configured to receive a nebulizer gas from the nebulizer gas source; and
an inlet configured to receive a gas from at least one of the first gas source and the second gas source; and
a controller operably coupled to the spray chamber to regulate fluid flow between the inlet of the spray chamber and at least the first gas source and the second gas source, the controller configured to access a memory device storing a chemical analysis schedule storing a list of chemical analyses to be performed by the analytical system, the controller also configured to access a memory device storing a gas flow setting corresponding to each chemical analysis of the list of chemical analyses, the controller configured to adjust a gas flow rate of each of the first gas source and the second gas source according to the gas flow setting in coordination with a next scheduled chemical analysis of the list of chemical analyses;
transferring the nebulizer gas to the nebulizer gas port;
accessing, via the controller, the memory device storing the chemical analysis schedule storing the list of chemical analyses to be performed by the analytical system;
accessing, via the controller, the memory device storing the gas flow setting corresponding to the next chemical analysis from the list of chemical analyses to be performed by the analytical system; and
regulating a flow of at least a first gas or a second gas to the gas inlet via the controller according to the gas flow setting prior to the next chemical analysis.

12. The method of claim 11, wherein regulating a flow of at least a first gas or a second gas to the gas inlet via the controller according to the gas flow setting includes permitting flow of the first gas from the first gas source to the gas inlet and preventing flow of the second gas from the second gas source to the gas inlet.

13. The method of claim 11, wherein regulating a flow of at least a first gas or a second gas to the gas inlet via the controller according to the gas flow setting includes preventing flow of the first gas from the first gas source to the gas inlet and permitting flow of the second gas from the second gas source to the gas inlet.

14. The method of claim 11, wherein regulating a flow of at least a first gas or a second gas to the gas inlet via the controller according to the gas flow setting includes preventing flow of the first gas from the first gas source to the gas inlet and preventing flow of the second gas from the second gas source to the gas inlet.

15. The method of claim 11, wherein regulating a flow of at least a first gas or a second gas to the gas inlet via the controller according to the gas flow setting includes permitting flow of the first gas from the first gas source to the gas inlet and permitting flow of the second gas from the second gas source to the gas inlet.

16. The method of claim 11, wherein the gas flow setting also includes at least one of a plasma condition type or a reaction cell gas type for a reaction cell of the analytical system.

17. The method of claim 11, further comprising:
adjusting a gas flow rate of the nebulizer gas to the nebulizer gas port in coordination with regulating the gas flow rate of at least the first gas or the second gas to the gas inlet to maintain a constant gas flow rate leaving the spray chamber.

18. The method of claim 17, wherein the gas flow rate of the nebulizer gas is higher than a combination of the gas flow rate of each of the first gas and the second gas.

19. The method of claim 11, wherein the controller is operably coupled to at least one of a multiport valve or a mass flow controller.

* * * * *